US011828756B2

(12) United States Patent
Adornetto et al.

(10) Patent No.: US 11,828,756 B2
(45) Date of Patent: Nov. 28, 2023

(54) LATERAL FLOW TEST ARRANGEMENT SUITABLE FOR DETECTION OF AN ANALYTE IN SALIVA

(71) Applicant: Feral GmbH, Berlin (DE)

(72) Inventors: Gianluca Adornetto, Berlin (DE); Fabio La Manna, Berlin (DE); Eirini Rapti, Berlin (DE)

(73) Assignee: Feral GmbH, Berlin (DE)

( * ) Notice: Subject to any disclaimer, the term of this patent is extended or adjusted under 35 U.S.C. 154(b) by 62 days.

(21) Appl. No.: 17/084,521

(22) Filed: Oct. 29, 2020

(65) Prior Publication Data

US 2021/0129138 A1     May 6, 2021

(30) Foreign Application Priority Data

Oct. 30, 2019  (EP) ...................... 19206125

(51) Int. Cl.
*G01N 33/543*   (2006.01)
*B01L 3/00*   (2006.01)

(52) U.S. Cl.
CPC ...... *G01N 33/54388* (2021.08); *B01L 3/5023* (2013.01); *B01L 2300/0825* (2013.01); *B01L 2300/12* (2013.01)

(58) Field of Classification Search
CPC .......... B01L 3/5023; B01L 2300/0825; B01L 2300/12; G01N 33/54306; G01N 33/54386; G01N 33/558
See application file for complete search history.

(56) References Cited

U.S. PATENT DOCUMENTS

| | | | |
|---|---|---|---|
| 6,924,153 B1* | 8/2005 | Boehringer | G01N 33/558 436/805 |
| 2002/0142291 A1 | 10/2002 | Bauer et al. | |
| 2003/0032196 A1* | 2/2003 | Zhou | G01N 33/54366 436/178 |
| 2006/0292700 A1 | 12/2006 | Wang et al. | |
| 2009/0170072 A1* | 7/2009 | Mink | A61B 10/0051 436/514 |
| 2010/0136566 A1* | 6/2010 | Mehra | G01N 33/54313 435/7.1 |
| 2011/0117636 A1 | 5/2011 | Bae et al. | |
| 2011/0136258 A1 | 6/2011 | Sambursky et al. | |
| 2012/0308444 A1 | 12/2012 | Zhu | |
| 2013/0017559 A1 | 1/2013 | Babu et al. | |

(Continued)

FOREIGN PATENT DOCUMENTS

| | | | | |
|---|---|---|---|---|
| CN | 201429617 Y | * | 3/2010 | |
| CN | 103314297 B | * | 10/2015 | ........... G01N 33/558 |

(Continued)

OTHER PUBLICATIONS

Extended European Search Report cited in EP 19206125 dated Apr. 21, 2020.

*Primary Examiner* — Dennis White
(74) *Attorney, Agent, or Firm* — Perkins Coie LLP; Jordan Becker

(57) ABSTRACT

Disclosed herein is a lateral flow test arrangement suitable for detection of an analyte in saliva. The arrangement can comprise a carrier and a sequence of different polymeric pads arranged on said carrier, wherein said sequence of polymeric pads comprises in flow direction.

24 Claims, 1 Drawing Sheet

(56) References Cited

U.S. PATENT DOCUMENTS

| | | | | |
|---|---|---|---|---|
| 2013/0309760 A1* | 11/2013 | Raj | ............... | G01N 33/76 435/287.7 |
| 2014/0017812 A1 | 1/2014 | Smith et al. | | |
| 2015/0293086 A1 | 10/2015 | Messmer et al. | | |
| 2017/0234866 A1 | 8/2017 | Hamad-Schifferli et al. | | |

FOREIGN PATENT DOCUMENTS

| | | | | |
|---|---|---|---|---|
| WO | 03042659 A2 | 5/2003 | | |
| WO | 2005098439 A2 | 10/2005 | | |
| WO | WO-2005116651 A2 * | 12/2005 | ....... | G01N 33/54386 |
| WO | 2008073222 A2 | 6/2008 | | |
| WO | 2012038820 A2 | 3/2012 | | |
| WO | 2013105090 A1 | 7/2013 | | |
| WO | WO-2015143196 A1 * | 9/2015 | ......... | G01N 21/8483 |
| WO | 2017029525 A1 | 2/2017 | | |
| WO | 2019081361 A1 | 5/2019 | | |

* cited by examiner

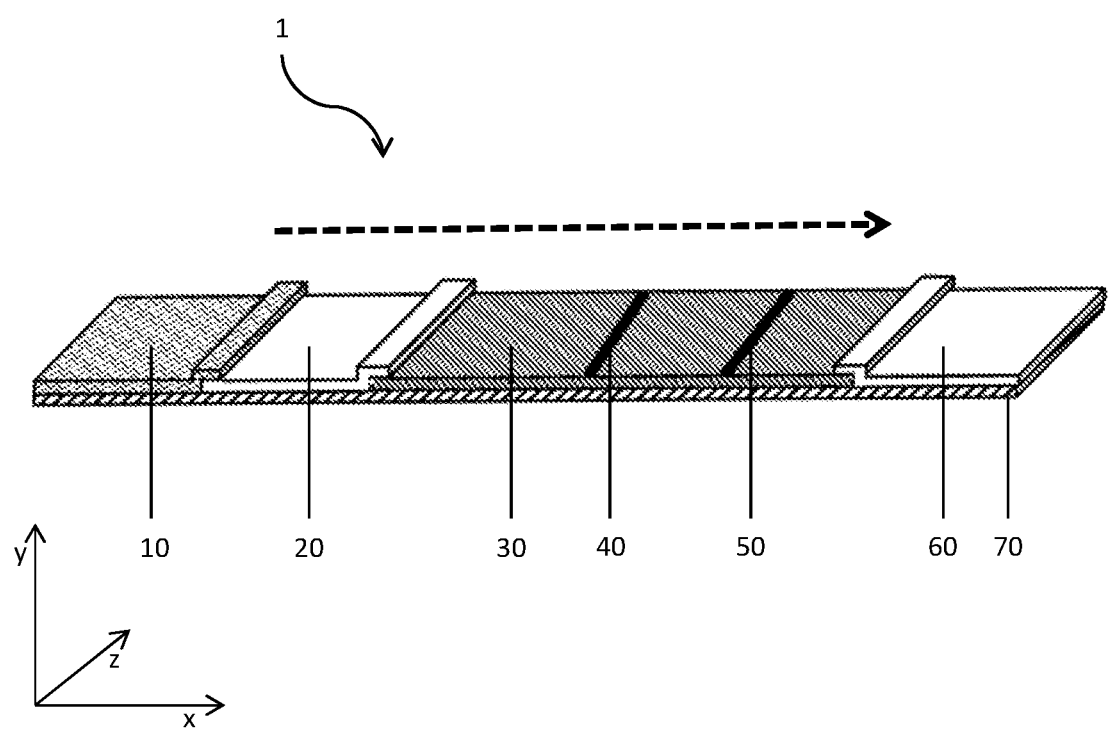

LATERAL FLOW TEST ARRANGEMENT SUITABLE FOR DETECTION OF AN ANALYTE IN SALIVA

TECHNICAL FIELD

The present invention relates to self-test immunochromatographic devices, in particular for use in fertility monitoring based on analysis of hormones derived from saliva.

BACKGROUND

A woman's monthly cycle is controlled by hormones. In particular, the hormones estrogen and progesterone control a woman's fertility. Measuring the progesterone levels and subsequently scoring the progesterone, allows the prediction of receptiveness period of the woman.

Lateral flow test arrangements (also lateral flow assays) constitute a cheap, fast and easy to handle self-test application with a broad patient acceptance. Ideally the use of such devices requires neither medical background of the user nor a clinical environment. That is, the application of the test must be simple and the test results must be unambiguous and reliable.

The general concept of lateral flow test arrangements has been widely described in literature. It can be summarized as followed:

To start a test run, a fluid sample (analyte fluid) containing the analyte of interest (e.g. a hormone in saliva) is applied to one end of the test strip, i.e. on the first polymeric pad so called sample pad, and moves by means of capillary forces through various functional areas of sequentially arranged polymeric pads along the test strip.

The second functional area is the conjugate area on the conjugate pad. It bears antibodies that can selectively interact with the analyte and which are fused with colored or fluorescent nanoparticles.

The analyte-bound nanoparticles then migrate through a third pad, the membrane pad, and across a detecting area which comprises one or more test lines and a control line. The test line is a primary read-out of the analyte of interest and consists of immobilized proteins that can bind the analyte-conjugated nanoparticle or the conjugate-nanoparticle itself to generate a signal that indicates the presence of the analyte sample, while the control line indicates the proper liquid flow through the strip.

At last, the analyte fluid migrates into a wicking pad adapted to absorb the excess and prevent backflow of the fluid which may distort the test result.

A variety of analyte samples can be tested by means of lateral flow test arrangements such as blood, plasma, serum, sweat, urine, and saliva. In the light of self-test applications sweat, urine and saliva are of particular interest. However, in these cases the sensitivity of the monitoring technique suffers i.e. from chromophore-aggregation due to poor fluid flow. In particular for saliva as sample fluid, the outcome of the test, that is the generation of unambiguous test line and control line signals, is negatively affected by varying sample viscosity, comparably low analyte concentrations and inaccurate sample volume.

SUMMARY

The present invention relates to a lateral flow test arrangement suitable for detection of an analyte in saliva and intends to solve one or more problems pointed out above.

The present invention relates to a lateral flow test arrangement suitable for detection of an analyte in saliva, the arrangement comprising a carrier and a sequence of different polymeric pads arranged on said carrier, wherein said sequence of polymeric pads comprises in flow direction:
- a sample pad composed of glass microfiber material, preferably glass microfiber material having a wicking rate of 3 to 5 s/2 cm, water absorption capacity of 35 to 40 mg/cm$^2$ and a density of 0.18 to 0.2 g/cm$^3$, and the sample pad comprising a sample area (adapted) for receiving a fluid sample to be analyzed;
- a conjugate pad comprising a conjugate area, said conjugate area comprising a conjugate, the conjugate area (adapted) for contacting the fluid sample with the conjugate, the conjugate comprising a binding moiety specific for the analyte and a detection moiety;
- a membrane pad comprising a detection area (adapted) for detection of analyte in the sample, the detection area comprising a test line and a control line arranged perpendicular to the flow direction, wherein the control line is arranged in flow direction downstream of the test line, wherein said test line comprises a compound which is bound specifically by the binding moiety of the conjugate (or a compound which binds specifically to the analyte), and wherein the control line comprises a compound which binds specifically to the binding moiety of the conjugate; and
- a wicking pad comprising a wicking area (adapted) for establishing fluid transport from the sample area to the wicking area.

According to one embodiment, the sample pad has been treated with solutions of a buffer salt and/or solutions of a surfactant prior to contacting the sample area with a fluid sample to be tested, preferably the buffer salt is selected from the group consisting of cetrimonium bromide (CTAB), chitosan, ethylenediaminetetraacetic acid (EDTA), CaCl$_2$), KCl, NaCl and 4-(2-hydroxyethyl)-1-piperazineethanesulfonic acid (HEPES) or may be combinations thereof; and preferably the surfactant is selected from the group consisting of Pluronic®F127 (PEG-PPG-PEG; Poly(ethylene glycol)-block-poly(propylene glycol)-block-poly(ethylene glycol); CAS Number 9003-11-6; PubChem Substance ID 24897874), Polysorbate 20 and bovine serum albumin (BSA) or may be combinations thereof.

In another embodiment, the carrier is a solid carrier, preferably a solid carrier comprising glass, paper, cardboard, polymer material or a combination thereof.

In one embodiment, the sample area has a length in flow direction of 10 to 20 mm, preferably 13 to 17 mm.

In another embodiment, the conjugate area has a length in flow direction of 15 to 30 mm, preferably 18 to 20 mm.

In one embodiment, the detection area has a length in flow direction of 15 to 30 mm, preferably 20 to 25 mm.

In one embodiment, the wicking area has a length in flow direction of 5 to 25 mm, preferably 13 to 20 mm.

In another embodiment, the sample pad overlaps the conjugate pad of the conjugate area to an extent of 2 to 10 mm in flow direction.

According to one embodiment, the conjugate pad overlaps the membrane pad of the detection area to an extent of 2 to 10 mm in flow direction.

In one embodiment, the wicking pad overlaps the membrane pad to an extent of 2 to 10 mm in flow direction. In another embodiment, the membrane pad overlaps the wicking pad to an extent of 2 to 10 mm against flow direction.

According to one embodiment, the conjugate pad overlaps the membrane pad to an extent of 2 to 10 mm in flow direction; and/or the conjugate pad is overlapped by the sample pad to an extent of 2 to 10 mm in flow direction.

In another embodiment, the test arrangement is adapted for detection of progesterone in saliva.

According to one embodiment, the binding moiety of the conjugate of the conjugate area comprises an antibody specific for progesterone, preferably a monoclonal [mouse] antibody, the compound of test line of the detection area comprises progesterone or part thereof including the epitope for the antibody of the binding moiety, preferably the compound of the test line is poly-streptavidin-biotin-progesterone, and the compound of the control line of the detection area comprises an antibody specific for the binding moiety of the conjugate.

In one embodiment, the detection moiety of the conjugate comprises carboxyl-modified gold particles, preferably carboxyl-modified gold nanoparticles with an average particle size of 20 to 60 nm.

In another embodiment, the conjugate pad is composed of glass fiber material, preferably a glass fiber material having a wicking rate of 2 to 2.5 s/2 cm, a water absorption capacity of 50 to 60 mg/cm$^2$ and a density of 0.18 to 0.2 g/cm$^3$.

In one embodiment, the membrane pad is composed of nitrocellulose material, preferably a nitrocellulose material with a wicking rate of 65 to 115 s/4 cm.

According to one embodiment, the wicking pad is composed of cellulose fiber material, preferably a cellulose fiber material having a absorption speed of 140 to 180 mm/30 min in and a thickness of 0.34 to 0.95 mm.

Further aspects of the present invention could be learned from the following description.

BRIEF DESCRIPTION OF THE DRAWING

Features will become apparent to those of ordinary skill in the art by describing in detail exemplary embodiments with reference to the attached drawings in which:

FIG. 1 illustrates a lateral flow test arrangement according to one embodiment of the present invention. The dashed arrow indicates the flow direction of the analyte fluid.

DETAILED DESCRIPTION

Reference will now be made in detail to embodiments, examples of which are illustrated in the accompanying drawings. Effects and features of the exemplary embodiments, and implementation methods thereof will be described with reference to the accompanying drawings. In the drawings, like reference numerals denote like elements, and redundant descriptions are omitted. As used herein, the term "and/or" includes any and all combinations of one or more of the associated listed items. Further, the use of "may" when describing embodiments of the present invention refers to "one or more embodiments of the present invention."

In the following description of embodiments of the present invention, the terms of a singular form may include plural forms unless the context clearly indicates otherwise.

In the drawings, the sizes of elements may be exaggerated for clarity. For example, in the drawings, the size or thickness of each element may be arbitrarily shown for illustrative purposes, and thus the embodiments of the present invention should not be construed as being limited thereto.

Hereinafter, example embodiments will be described in more detail with reference to the accompanying drawings, in which like reference numbers refer to like elements throughout. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques which are not necessary to those having ordinary skill in the art for a complete understanding of the aspects and features of the present disclosure may not be described.

As used herein, the term "substantially," "about," and similar terms are used as terms of approximation and not as terms of degree, and are intended to account for the inherent deviations in measured or calculated values that would be recognized by those of ordinary skill in the art. Further, if the term "substantially" is used in combination with a feature that could be expressed using a numeric value, the term "substantially" denotes a range of +/−5% of the value centered on the value. Further, the use of "may" when describing embodiments of the present invention refers to "one or more embodiments of the present invention." Herein, the terms "upper" and "lower" are defined according to the y-axis. For example, the pad is positioned at the upper part of the y-axis, whereas the carrier is positioned at the lower part thereof.

The unit wt. % is understood as percentage by weight according to the mass fraction of a substance within a mixture multiplied with a denominator of 100.

The "wicking rate" denotes the rate of movement of a liquid laterally through a filter material. The rate can be expressed as the time taken for liquid to move a certain distance or the distance moved in a certain time.

Further, the direction of the analyte fluid flow (flow direction) is indicated by dashed arrows in the figures. Herein, the terms "upstream" and "downstream" are defined according to the flow direction of the analyte fluid along the x-axis. For example, the test line is positioned upstream from the control line, i.e. the position of the test line is at smaller x-values; but downstream from the sample area.

Introduced herein is a lateral flow test arrangement suitable for detection of an analyte in saliva. The arrangement can comprise a carrier and a sequence of different polymeric pads arranged on said carrier. The sequence of polymeric pads can comprise in flow direction.

A sample pad composed of glass microfiber material, preferably glass microfiber material having a wicking rate of 3 to 5 s/2 cm, water absorption capacity of 35 to 40 mg/cm$^2$ and a density of 0.18 to 0.2 g/cm$^3$ comprising a sample area (adapted) for receiving a fluid sample to be analyzed; a conjugate pad comprising a conjugate area, said conjugate area comprising a conjugate, the conjugate area (adapted) for contacting the fluid sample with the conjugate, the conjugate comprising a binding moiety specific for the analyte and a detection moiety; a membrane pad comprising a detection area (adapted) for detection of analyte in the sample, the detection area comprising a test line and a control line arranged perpendicular to the flow direction, wherein the control line is arranged in flow direction downstream of the test line, wherein said test line comprises a compound which is bound specifically by the binding moiety of the conjugate (or a compound which binds specifically to the analyte), and wherein the control line comprises a compound which binds specifically to the binding moiety of the conjugate; and a wicking pad comprising a wicking area (adapted) for establishing fluid transport from the sample area to the wicking area.

The following reference numerals and corresponding elements are used in this description:
1 lateral flow test arrangement
10 sample pad
20 conjugate pad
30 membrane pad
40 test line
50 control line
60 wicking pad
70 carrier As shown in FIG. 1, the lateral flow test arrangement 1 comprises sequentially arranged areas resulting from overlapping pads that are laminated on a carrier 70 for better stability and handling. The carrier 70 may be a solid carrier such as a backing card or a backing foil. Preferably, the solid carrier 70 comprises glass, paper, cardboard, polymer material or a combination thereof. The carrier may be rectangular, trapezoid or circular.

The width (perpendicular to flow direction) of the lateral flow test arrangement 1 (the strip width) may be 3 to 10 mm, preferably 5 to 8 mm.

The surface geometry of the polymeric pad may be rectangular or trapezoid, wherein in the case of a trapezoid surface geometry, the parallel sides are perpendicular to flow direction.

The analyte fluid is applied on the sample pad 10. The sample pad 10 may be (pre-) treated with a (aqueous) buffer salt solution and/or a (aqueous) surfactant solution. The (pre-) treatment of the sample pad 10 by means of buffer salt and/or surfactant solutions results in reduced aggregation of the conjugate and an improved analyte fluid flow.

The dissolved buffer salt for (pre-) treating the sample pad 10 may be selected from the group consisting of cetrimonium bromide (CTAB), chitosan, ethylenediaminetetraacetic acid (EDTA), $CaCl_2$), KCl, NaCl and 4-(2-hydroxyethyl)-1-piperazineethanesulfonic acid (HEPES) or may be combinations thereof. Preferably, the (pre-) treating of the sample pad 10 comprises treating with (aqueous) solutions of NaCl and 4-(2-hydroxyethyl)-1-piperazineethanesulfonic acid (HEPES). The treatment improves the fluid sample flow of saliva with higher viscosity and yields sufficiently colored test and control lines, i.e. the treatment improves the reliability of the test method. Improving the fluid flow of high-viscosity samples, the treatment normalizes the behavior between different samples.

The (dissolved) surfactant for (pre-) treating the sample pad 10 may be selected from the group consisting of Pluronic®F127 (CAS Number 9003-11-6), Polysorbate 20 (Tw-20, CAS Number 9005-64-5) and bovine serum albumin (BSA) or may be combinations thereof. Preferably, the surfactant solution for (pre-) treating the sample pad 10 comprises Pluronic®F127 (CAS Number 9003-11-6). The treatment suppresses undesired conjugate aggregation on the conjugate pad or sample pad.

Preferably, the sample pad has been (pre-) treated with (aqueous) solutions of 4-(2-hydroxyethyl)-1-piperazineethanesulfonic acid, NaCl and Pluronic®F127 prior to contacting the sample area with a fluid sample to be tested. Preferably, the sample pad has been (pre-) treated with (aqueous) buffer solutions comprising 4-(2-hydroxyethyl)-1-piperazineethane-sulfonic acid in a concentration range of 10 to 60 mM prior to contacting the sample area with a fluid sample to be tested. Preferably, the sample pad has been (pre-) treated with (aqueous) buffer solutions comprising NaCl in a concentration range of 0.5 to 3 M prior to contacting the sample area with a fluid sample to be tested. Preferably, the sample pad has been (pre-)treated with (aqueous) surfactants solutions comprising Pluronic®F127 in a weight percent range of 0.5 to 1 wt. % prior to contacting the sample area with a fluid sample to be tested. Abovementioned treatment of the sample pad improves the fluid sample flow of saliva with higher viscosity and to yield sufficiently coloured (unambiguous) test and control lines without undesired conjugate aggregation on the conjugate pad or sample pad. That is the treatment improves the reliability of the test method. As it allows the full release of the conjugate, the abovementioned treatment improves also the sensitivity of the test method.

In flow direction the length of the sample area may be 10 to 20 mm, preferably 13 to 17 mm, most preferably 14 to 15 mm. The length (in flow direction) of sample area refers to the length of the sample pad minus the length of the overlap area with the conjugate pad 20. The length (in flow direction) of sample area within the abovementioned range allows the absorption of an optimal sample volume in order to provide ideal conditions for sample (pre-) treatment and filtration.

In one embodiment the surface geometry of the sample pad may be rectangular. In another embodiment the surface geometry of the sample pad may be trapezoid, wherein the parallel sides of the trapezoid are perpendicular to flow direction and the longer parallel side is downstream the shorter parallel side or the shorter parallel side is downstream the longer parallel side, preferably the longer parallel side is downstream the shorter parallel side.

Further the sample pad 10 may overlap the conjugate pad 20 to an extent of 2 to 10 mm in flow direction in order to improve the fluid transfer. Preferably, the sample pad 10 may constitute the upper part of the overlap and the conjugate pad 20 may constitute the lower part of the overlap. The conjugate pad 20 may alternatively constitute the upper part of the overlap and the sample pad 10 may constitute the lower part of the overlap.

Once the analyte fluid has been applied to the sample area of the sample pad 10, the analyte fluid migrates from the sample pad 10 into and through the conjugate pad 20.

The conjugate pad 20 may be composed of (porous) glass fiber material, preferably a glass fiber material having a wicking rate of 2 to 2.5 s/2 cm, a water absorption capacity of 50 to 60 mg/cm$^2$ and a density of 0.18 to 0.2 g/cm$^3$. The specific wicking rate, water absorption capacity and density provide an improved fluid flow and reduce undesired conjugate aggregation on the conjugated pad. Use of a glass fiber material allows the full release of the conjugate with a viscous matrix as saliva.

In flow direction the length of the conjugate area may be 15 to 30 mm, preferably 18 to 20 mm. The length (in flow direction) of conjugate area refers to the length of the conjugate pad minus the length of the overlap areas with the sample pad 10 and the membrane pad 30. The length (in flow direction) of conjugate area within the abovementioned range provides sufficient conjugate to be dissolved in the fluid sample and sufficient equilibration time for the analyte to interact with the conjugate. The overlap areas with the sample pad and the membrane pad allow the complete filtration and the complete treatment of the sample material, helping the reduction of the viscosity.

The conjugate pad 20 of the conjugate area may overlap the membrane pad 30 of the detection area to an extent of 2 to 10 mm in order to improve the fluid transfer. Preferably, the conjugate pad 20 may constitute the upper part of the overlap and the membrane pad 30 may constitute the lower part of the overlap. The membrane pad 30 may alternatively constitute the upper part of the overlap and conjugate pad 20 may constitute the lower part of the overlap.

Further, the conjugate pad 20 comprises a conjugate. The conjugate is a molecule that comprises a detection moiety and a binding moiety specific for the analyte.

The detection moiety of the conjugate may be colored particles, preferably carboxyl-modified gold nanoparticles with an average particle size of 20 to 60 nm, preferably 30 to 40 nm.

The binding moiety of the conjugate may be an antibody specific for progesterone, preferably a monoclonal [mouse] antibody.

The analyte fluid, i.e. unbound conjugate together with the conjugate bound to the analyte, both in the fluid, subsequently migrates from the conjugate pad 20 into membrane pad 30.

The membrane pad 30 may be a porous membrane, preferably being made of nitrocellulose. Preferably, the membrane pad 30 is being made of a nitrocellulose material with a wicking rate of 65 to 115 s/4 cm.

In flow direction the length of the detection area may be 15 to 30 mm, preferably 20 to 25 mm. The length (in flow direction) of detection area refers to the length of the membrane pad minus the length of the overlap areas with the conjugate pad 20 and the wicking pad 60.

The detection area comprises a test line 40 and a control line 50, which are perpendicular arranged to the flow direction. That is, the fluid sample cannot migrate through the membrane pad without passing the test line 40 and the control line 50. The control line 50 is positioned downstream from the test line 40 on the detection area of the membrane pad 30.

The test line 40 (abbrev. TL) comprises an (immobilized) compound that specifically binds with the binding moiety of the conjugate. In other words, the compound feasible to specifically bind with the binding moiety of the conjugate is immobilized on the detection area of the membrane pad 30 in form of the test line 40. Preferably, the (immobilized) compound of the test line 40 comprises progesterone or part thereof including an epitope for the antibody of the binding moiety. The epitope is a binding site on the (immobilized) compound of the test line 40 to which a complementary binding moiety of the conjugate may specifically bind. That is, if an antibody, e.g. progesterone, is present in the analyte fluid, the antibody will compete with the conjugate to bind with the compound of the test line 40. Preferably, the compound of the test line 40 is poly-streptavidin-biotin-progesterone.

Recognition of the analyte results in an appropriate response on the test line 40, which may be the absence of a signal in case the test line 40 comprises an (immobilized) compound that specifically binds with the binding moiety of the conjugate.

In another embodiment, the test line 40 comprises a compound that specifically binds with the analyte bound to the conjugate. Here, the recognition of the analyte results in an appropriate response on the test line 40, which may be the occurrence of a signal.

The control line 50 (CL) comprises a compound that binds specifically to the binding moiety of the conjugate. In other words, the compound feasible to specifically bind with the binding moiety of the conjugate is immobilized on the detection area of the membrane pad 30 in form of the control line 50. Preferably, the compound of the control line 50 is an antibody that specifically binds to the binding moiety of the conjugate. A response on the control line 50 indicates the proper fluid flow through the strip.

In order to maintain the fluid flow, to wick the excess reagents and to prevent backflow of the fluid, a wicking pad 60 is attached downstream of membrane pad 30.

In flow direction the length of the wicking area may be 5 to 25 mm, preferably 13 to 20 mm, most preferably 14 to 17 mm. The length (in flow direction) of wicking area refers to the length of the wicking pad 60 minus the length of the overlap area with the membrane pad 30.

The wicking pad 60 may overlap the membrane pad 30 to an extent of 2 to 10 mm against flow direction in order to prevent backflow of the fluid sample. Preferably, the wicking pad 60 may constitute the upper part of the overlap and the membrane pad 30 may constitute the lower part of the overlap. The membrane pad 30 may alternatively constitute the upper part of the overlap and the wicking pad 60 may constitute the lower part of the overlap.

Sample Pad Evaluation with Anti Progesterone Gold Particle Conjugate on Full Strips with Conjugate Pad and Sample Pad Experiment 1: Examination of Fluid Sample Flow Preparation method: 1. Method: 1. Prepare Strips (full 80 mm Strips with 30 mm conjugate pad and 20 mm sample pad). Laminate the membranes onto 80 mm backing cards 38 mm from the bottom of the card. Laminate 18 mm wicking pad (chromatographic paper) onto top of backing card with a 2 mm overlap onto membrane. Laminate the respective 30 mm conjugate pad (glass fiber pad) overlapping the membrane pad (nitrocellulose membrane striped with 2 mg/mL Poly-Streptavidinbiotin-Progesterone TL with a 0.5 mg/mL Goat Anti Mouse CL (Position 9 mm TL and 14 mm CL)) by 2 mm and down. Laminate the respective 20 mm sample pad from the bottom of the card up overlapping the membrane by 8 mm. Cut strips to 5 mm width.

2. Prepare saliva sample for evaluation. To 1000 µl of fresh saliva add 100 µl of 5 M NaCl solution (in DI water) and 50 µl of 10 wt. % Pluronic®F127 (in DI water). To 1000 µL of fresh saliva add 100 µl of 5 M NaCl solution (in DI water) and 100 µl of 10 wt. % Tw-20 (in DI water).

Test Method: 1. Lay strip flat on bench top, slowly add 120 µl of saliva sample to the bottom of the sample pad and let wick up. 2. Run strips for 15 minutes.

Evaluated sample pads: microglass fiber pad, rayon/cotton pad, glass fiber pad type 1, glass fiber pad type 2, PE/PP Sample Pad, glass fiber pad type 3, Fusion 5 (GE).

Table 1 shows the TL/CL ratios from evaluating different sample pads. Fusion 5 and microglass fiber pad both show good flow of saliva and full release of conjugate from the conjugate pad. Tw-20 treatment shows stronger signal than Pluronic®F127 treatment.

TABLE 1

Sample pad evaluation on fluid sample flow. TL = test line signal intensity; CL = control line signal intensity; signal ratio TL/CL.

| Sample Treatment | Sample Pad | TL/CL | Comment |
| --- | --- | --- | --- |
| 1 wt.% Tw-20, 0.5M NaCl | rayon/cotton pad | 0.95 | * |
| | glass fiber pad type 1 | 1.20 | * |
| | glass fiber pad type 2 | 1.02 | * |
| | Sample Pad PE/PP | 1.16 | * |
| | glass fiber pad type 3 | 1.01 | * |
| | Fusion 5 (GE) | 1.18 | |
| | micro glass fiber pad | 0.87 | |

TABLE 1-continued

Sample pad evaluation on fluid sample flow. TL = test line signal
intensity; CL = control line signal intensity; signal ratio TL/CL.

| Sample Treatment | Sample Pad | TL/CL | Comment |
|---|---|---|---|
| 0.5 wt. % Pluronic ® F127, 0.5M NaCl | rayon/cotton pad | 0.75 | * |
| | glass fiber pad type 1 | 1.25 | * |
| | glass fiber pad type 2 | 0.64 | * |
| | Sample Pad PE/PP | 0.78 | * |
| | glass fiber pad type 3 | 0.64 | * |
| | Fusion 5 (GE) | 1.02 | |
| | micro glass fiber pad | 1.00 | |

Experiment 2: Examination of Signal Dependency on Progesterone Concentration

Table 2 shows the TL and CL peak heights and TL/CL ratios from evaluating different sample pads with different saliva treatments. The results show correlation with both pads tested with Tw-20 sample treatment and only with the microglass fiber pad for the Pluronic® F127 sample treatment.

TABLE 2

Sample pad evaluation referring the signal dependency on
progesterone concentration. TL = test line signal intensity;
CL = control line signal intensity; signal ratio TL/CL.

| Sample Treatment | Sample Pad | Progesterone Conc. (pg/mL) | TL/CL |
|---|---|---|---|
| 1 wt. % Tw-20, 0.5M NaCl | Fusion 5 (GE) | 0 | 0.88 |
| | | 50 | 0.82 |
| | | 100 | 0.78 |
| | | 200 | 0.71 |
| | | 400 | 0.53 |
| | | 800 | 0.36 |
| | Micro glass fiber pad | 0 | 0.69 |
| | | 50 | 0.67 |
| | | 100 | 0.59 |
| | | 200 | 0.51 |
| | | 400 | 0.40 |
| | | 800 | 0.31 |
| 0.5 wt. % Pluronic ® F127, 0.5M NaCl | Fusion 5 (GE) | 0 | 0.91 |
| | | 50 | 0.99 |
| | | 100 | 0.85 |
| | | 200 | 0.97 |
| | | 400 | 0.81 |
| | | 800 | 0.87 |
| | micro glass fiber pad | 0 | 0.62 |
| | | 50 | 0.59 |
| | | 100 | 0.61 |
| | | 200 | 0.44 |
| | | 400 | 0.33 |
| | | 800 | 0.25 |

Experiment 3: Examination of Fluid Sample Flow on Test Strips with Poor Flowing *Salvia* Sample Method: 1. Prepare Strips (full 80 mm Strips with 30 mm conjugate pad and 20 mm sample pad). Laminate the membranes onto 80 mm backing cards 38 mm from the bottom of the card. Laminate 18 mm wicking pad (chromatographic paper) onto top of backing card with a 2 mm overlap onto membrane. Laminate the respective 30 mm conjugate pad overlapping the membrane pad (CN95 nitrocellulose membrane striped with 2 mg/mL Poly-Streptavidinbiotin-Progesterone TL with a 0.5 mg/mL Goat Anti Mouse CL (Position 9 mm TL and 14 mm CL)) by 2 mm and down. Laminate the respective 20 mm sample pad from the bottom of the card up overlapping the membrane by 8 mm. Cut strips to 5 mm width.

2. Prepare Saliva for evaluation. To 500 µL of fresh saliva add 50 µL of 5 M NaCl and 25 µL 10 wt. % Pluronic®F127, vortex to mix. To 500 µL of fresh saliva add 50 µL of 5 M NaCl and 50 µL 10 wt. % Tw-20, vortex to mix.

Test Method: (Full Strip in saliva, dry conjugate, 80 mm Strip) 1. Lay strip flat on bench top, slowly add 120 µL of saliva sample to the bottom of the sample pad and let wick up. 2. Run strips for 15 minutes.

Table 3 shows the TL and CL peak heights evaluating different saliva treatments with a poor flowing saliva sample in full strip format with a varying conjugate pads and sample pads. The results show that the conjugate is fully released from the conjugate pad and signal is increased when combing the glass fiber pad type 1 (conjugate pad) with microglass fiber pad (sample pad) compared to all other tested variations with PE/PP HRM Fiber, High Density pad and glass fiber pad type 2. In particular, the fluid sample flow of saliva with higher viscosity is improved when using the microglass fiber pad as sample pad.

TABLE 3

Evaluation fluid sample flow of poor flow sample on varying
sample pads and conjugate pads.

| Conjugate pad | Sample Pad | Sample | Sample Treatment | Comment |
|---|---|---|---|---|
| Glass fiber pad type 1 | PE/PP HRM Fiber, High Density | Poor Flowsaliva sample | 1 wt. % Tw-20, 0.5M NaCl | a |
| | | | 0.5 wt. % Pluronic ® F127, 0.5M NaCl | a |
| | Microglass fiber pad | | 1 wt. % Tw-20, 0.5M NaCl | |
| | | | 0.5 wt. % Pluronic ® F127, 0.5M NaCl | |
| Glass fiber pad type 2 | PE/PP HRM Fiber, High Density | | 1 wt. % Tw-20, 0.5M NaCl | a |
| | | | 0.5 wt. % Pluronic ® F127, 0.5M NaCl | a |
| | Microglass fiber pad | | 1 wt. % Tw-20, 0.5M NaCl | a, b |
| | | | 0.5 wt. % Pluronic ® F127, 0.5M NaCl | a, b |

What is claimed is:

1. A lateral flow test arrangement suitable for detection of an analyte in saliva, the arrangement comprising a carrier and a sequence of different polymeric pads arranged on said carrier, wherein said sequence of polymeric pads comprises in flow direction:
   a sample pad composed of glass microfiber material having a wicking rate of 3 to 5 s/2 cm, water absorption capacity of 35 to 40 mg/cm$^2$ and a density of 0.18 to 0.2 g/cm$^3$, and the sample pad comprising a sample area for receiving a fluid sample to be analyzed;
   a conjugate pad comprising a conjugate area, said conjugate area comprising a conjugate, the conjugate area for contacting the fluid sample with the conjugate, the conjugate comprising a binding moiety specific for the analyte and a detection moiety, wherein the detection moiety of the conjugate comprises carboxyl-modified gold particles;
   a membrane pad comprising a detection area for detection of analyte in the sample, the detection area comprising a test line and a control line arranged perpendicular to the flow direction, wherein the control line is arranged in flow direction downstream of the test line, wherein said test line comprises a compound which is bound specifically by the binding moiety of the conjugate or a compound which binds specifically to the analyte, and wherein the control line comprises a compound which binds specifically to the binding moiety of the conjugate; and a wicking pad comprising a wicking area for establishing fluid transport from the sample area to the wicking area;

wherein the sample pad has been treated with solutions of a buffer salt and solutions of a surfactant prior to contacting the sample area with a fluid sample to be tested;

wherein the buffer salt is a member or a combination of members of the group consisting of cetrimonium bromide (CTAB), chitosan, $CaCl_2$), KCl, NaCl and 4-(2-hydroxyethyl)-1-piperazineethanesulfonic acid (HEPES); and wherein the surfactant is the substance having CAS number 9003-11-6.

2. The lateral flow test arrangement of claim 1, wherein the carrier is a solid carrier.

3. The lateral flow test arrangement of claim 2, wherein the carrier is a solid carrier comprising glass, paper, cardboard, polymer material, or a combination thereof.

4. The lateral flow test arrangement of claim 1, wherein the sample area has a length in flow direction of 10 to 20 mm.

5. The lateral flow test arrangement of claim 4, wherein the conjugate area has a length in flow direction of 15 to 30 mm.

6. The lateral flow test arrangement of claim 5, wherein the detection area has a length in flow direction of 15 to 30 mm.

7. The lateral flow test arrangement of claim 6 wherein the wicking area has a length in flow direction of 5 to 25 mm.

8. The lateral flow test arrangement of claim 1, wherein the conjugate area has a length in flow direction of 15 to 30 mm.

9. The lateral flow test arrangement of claim 1, wherein the detection area has a length in flow direction of 15 to 30 mm.

10. The lateral flow test arrangement of claim 1, wherein the wicking area has a length in flow direction of 5 to 25 mm.

11. The lateral flow test arrangement of claim 1, wherein the conjugate pad overlaps the membrane pad to an extent of 2 to 10 mm in flow direction and/or the conjugate pad is overlapped by the sample pad to an extent of 2 to 10 mm in flow direction.

12. The lateral flow test arrangement of claim 1, wherein the wicking pad overlaps the membrane pad to an extent of 2 to 10 mm against flow direction.

13. The lateral flow test arrangement of claim 1, wherein the test arrangement is adapted for detection of progesterone in saliva.

14. The lateral flow test arrangement of claim 1, wherein the binding moiety of the conjugate of the conjugate area comprises an antibody specific for progesterone, the compound of test line of the detection area comprises progesterone or part thereof including the epitope for the antibody of the binding moiety, and the compound of the control line of the detection area comprises an antibody specific for the binding moiety of the conjugate.

15. The lateral flow test arrangement of claim 14, wherein the binding moiety of the conjugate of the conjugate area comprises a monoclonal [mouse] antibody.

16. The lateral flow test arrangement of claim 14, wherein the compound of the test line is poly-streptavidin-biotin-progesterone.

17. The lateral flow test arrangement of claim 1, wherein the detection moiety of the conjugate comprises carboxyl-modified gold nanoparticles with an average particle size of 20 to 60 nm.

18. The lateral flow test arrangement of claim 1, wherein the conjugate pad is composed of a glass fiber material.

19. The lateral flow test arrangement of claim 18, wherein the conjugate pad is composed of a glass fiber material having a wicking rate of 2 to 2.5 s/2 cm, a water absorption capacity of 50 to 60 $mg/cm^2$ and a density of 0.18 to 0.2 $g/cm^3$.

20. The lateral flow test arrangement of claim 1, wherein the membrane pad is composed of a nitrocellulose material.

21. The lateral flow test arrangement of claim 20, wherein the membrane pad is composed of a nitrocellulose material with a wicking rate of 65 to 115 s/4 cm.

22. The lateral flow test arrangement of claim 1, wherein the wicking pad is composed of a cellulose fiber material.

23. The lateral flow test arrangement of claim 22, wherein the wicking pad is composed of a cellulose fiber material having an absorption speed of 140 to 180 mm/30 min and a thickness of 0.34 to 0.95 mm.

24. The lateral flow test arrangement of claim 1, wherein the solutions of a surfactant comprise the substance having CAS number 9003-11-6 in a weight percent range of 0.5 to 1 wt. %.

* * * * *